US00PP10901P

United States Patent [19]

VandenBerg

[11] Patent Number: Plant 10,901

[45] Date of Patent: May 18, 1999

[54] CHRYSANTHEMUM PLANT NAMED 'JEAN'

[75] Inventor: Cornelis P. VandenBerg, Salinas, Calif.

[73] Assignee: Yoder Brothers, Inc., Barberton, Ohio

[21] Appl. No.: 08/990,907

[22] Filed: Dec. 15, 1997

[51] Int. Cl.[6] ..... A01H 5/00

[52] U.S. Cl. ..... Plt./76

[58] Field of Search ..... Plt./76, 80

*Primary Examiner*—Howard J. Locker

*Attorney, Agent, or Firm*—C. A. Whealy

[57] ABSTRACT

A distinct cultivar of Chrysanthemum plant named 'Jean', characterized by its uniformly mounded plant habit; decorative spray-type inflorescences that are about 5.3 cm in diameter; attractive and numerous lavender ray florets; numerous inflorescences per plant; and excellent garden performance.

1 Drawing Sheet

The present invention relates to a new and distinct cultivar of Chrysanthemum plant, botanically known as *Dendranthema grandiflora* and referred to bythe cultivar name 'Jean'.

The new cultivar is a product of a planned breeding program conducted by the inventor in Salinas, Calif. The objective of the breeding program is to create new garden-type Chrysanthemum cultivars having inflorescences with desirable inflorescence forms and floret colors and good garden performance.

The new cultivar originated from a cross made by the inventor in November, 1991, of the *Dendranthema grandiflora* cultivar 'Sophia' (disclosed in U.S. Plant Pat. No. 9,558) as the female, or seed, parent with the *Dendranthema grandiflora* cultivar 'Emily' (disclosed in U.S. Plant Pat. No. 7,754) as the male, or pollen, parent.

The cultivar 'Jean' was discovered and selected by the inventor as a flowering plant within the progeny of the stated cross in a controlled environment in Salinas, Calif., in September, 1992. The selection of this plant was based on its desirable inflorescence form and floret colors and excellent garden performance.

Asexual reproduction of the new cultivar by terminal cuttings taken in a controlled environment in Salinas, Calif., has shown that the unique features of this new Chrysanthemum are stable and reproduced true to type in successive generations.

The cultivar 'Jean' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Jean'. These characteristics in combination distinguish 'Jean' as a new and distinct cultivar:

1. Uniformly mounded plant habit.
2. Decorative spray-type inflorescences that are about 5.3 cm in diameter.
3. Attractive and numerous lavender ray florets.
4. Numerous inflorescences per plant.
5. Excellent garden performance.

The new Chrysanthemum is similar in ray floret color and form to the Chrysanthemum cultivar 'Sophia' (disclosed in U.S. Plant Pat. No. 9,558). However in side-by-side comparisons in Leaminton, Ontario, Canada, under commercial practice, plants of the new Chrysanthemum differed from plants of the cultivar 'Sophia' in the following characteristics:

1. Plants of the new Chrysanthemum are taller and more outwardly spreading than plants of the cultivar 'Sophia'.

2. After pinching, plants of the new Chrysanthemum develop more lateral branches than plants of the cultivar 'Sophia'.
3. Plants of the new Chrysanthemum flower slightly later than plants of the cultivar 'Sophia'.
4. Plants of the new Chrysanthemum have smaller inflorescences than plants of the cultivar 'Sophia'.
5. Ray florets of plants of the new Chrysanthemum have longer corolla tubes than ray florets of plants of the cultivar 'Sophia'.
6. The apices of ray florets of plants of the new Chrysanthemum are dentate whereas the apices of ray florets of plants of the cultivar 'Sophia' are rounded.
7. Ray florets of plants of the new Chrysanthemum are similar to slightly lighter in color than ray florets of plants of the cultivar 'Sophia'.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Jean'.

The photograph at the bottom of the sheet comprises a close-up view of typical inflorescences of the cultivar 'Jean'.

These photographs show the colors as true as it is reasonably possible to obtain in colored reproduction of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One unrooted cutting was directly stuck in a 15-cm container and plants were grown in a greenhouse with night interruption lighting for two weeks during late May/early June. At the end of the night interruption lighting period, plants were pinched (terminal apices removed). Three days later, plants were moved into an outdoor production area. Plants flowered about eight weeks later. Measurements and numerical values represent averages for typical flowering containers.

Botanical classification: *Dendranthema grandiflora* cultivar 'Jean'.

Commercial classification: Decorative spray-type garden Chrysanthemum.

Parentage:

*Male or pollen parent.*—*Dendranthema grandiflora* cultivar 'Sophia', disclosed in U.S. Plant Pat. No. 9,558.

*Female or seed parent.*—*Dendranthema grandiflora* cultivar 'Emily', disclosed in U.S. Plant Pat. No. 7,754.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative spray-type garden Chrysanthemum. Inverted triangle. Stems initially upright, then spreading giving a uniformly mounded appearance to the plant. Freely branching; about eight lateral branches develop after removal of terminal apex (pinching). Numerous secondary lateral branches develop at every node.

*Plant height.*—About 29.5 cm.

*Foliage description.*—Leaf arrangement: Alternate. Length: About 5 cm. Width: About 3.75 cm. Apex: Mucronate. Base: Attenuate. Margin: Palmately lobed, sinuses parallel. Texture: Upper and lower surfaces slightly pubescent. Veins prominent on lower surface. Petiole length: About 1.8 cm. Color: Young foliage upper surface: 147A. Young foliage lower surface: 147B. Mature foliage upper surface: 147A. Mature foliage lower surface: 147B. Venation upper surface: 147B. Venation lower surface: 147B.

Inflorescence description:

*Appearance.*—Decorative spray-type inflorescence form. Inflorescences borne on terminals above foliage, arising from leaf axils. Disk and ray florets arranged acropetally on a capitulum. One inflorescence per terminal with numerous inflorescences per plant.

*Flowering response.*—Under natural conditions, plants flower in the autumn. Plants exposed to 1.5 to 2 weeks of long day/short night conditions after planting followed by short day/long night conditions flower about 55 days later.

*Inflorescence size.*—Diameter: About 5.3 cm. Depth (height): About 2 cm.

*Ray florets.*—Shape: Spatulate; initially cupped, then recurved. Length: About 2.5 cm. Width: About 6.5 mm. Apex: Mostly dentate. Margin: Entire. Texture: Smooth, glabrous. Orientation: Slightly upright to recurved with development. Number of ray florets per inflorescence: About 220. Color: When opening: White. Opened inflorescence: Upper surface: 75D developing darker to 75A. Lower surface: 75B/75C.

*Disc florets.*—None observed.

*Peduncle.*—Aspect: Flexible, angled about 45 to 50° to the stem. Length: First peduncle: About 6 cm. Fourth peduncle: About 8 cm. Texture: Pubescent. Color: 143A.

*Reproductive organs.*—Androecium: None observed. Gynoecium: Present on ray florets.

Disease resistance: No known Chrysanthemum diseases observed to date on plants grown under commercial production conditions.

Seed production: Seed production has not been observed.

It is claimed:

1. A new and distinct cultivar of Chrysanthemum plant named 'Jean', as illustrated and described.

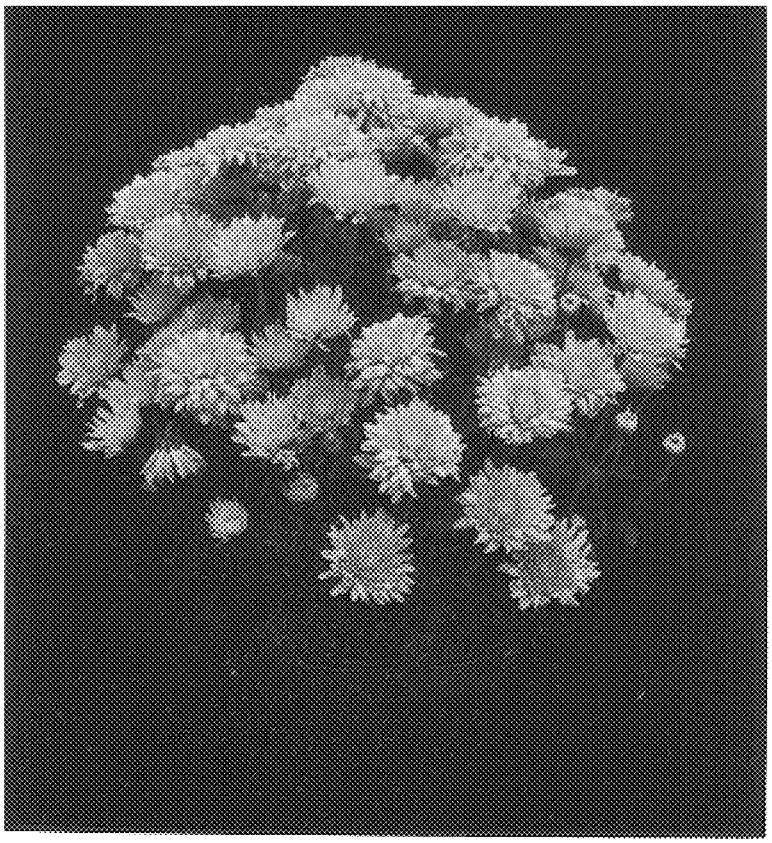
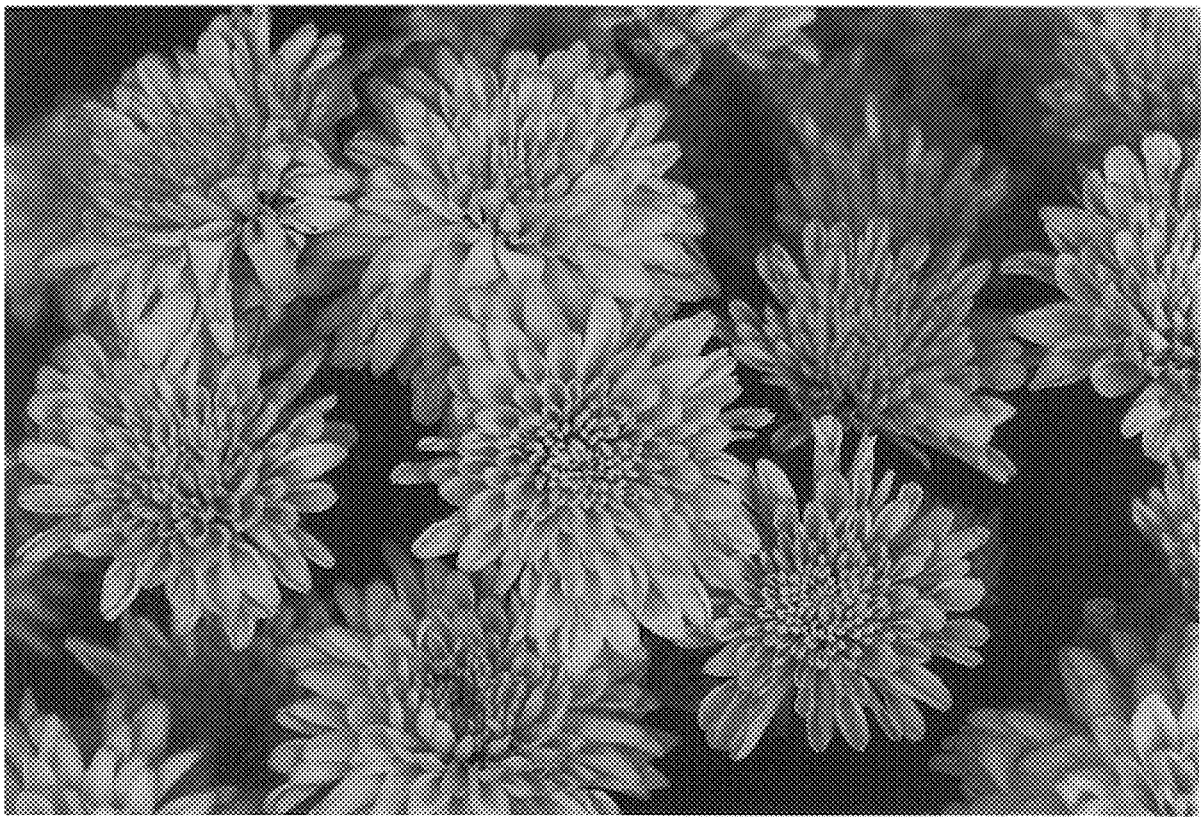

* * * * *